(12) United States Patent
Reed

(10) Patent No.: US 6,534,035 B1
(45) Date of Patent: Mar. 18, 2003

(54) METHODS OF INHIBITING CLOT FORMATION

(75) Inventor: Guy L. Reed, Winchester, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/321,969

(22) Filed: May 28, 1999

Related U.S. Application Data

(60) Provisional application No. 60/087,218, filed on May 29, 1998.

(51) Int. Cl.$^7$ .......................... A61K 51/00; C07K 14/00

(52) U.S. Cl. ........................ 424/1.69; 530/380; 530/350

(58) Field of Search ................................ 530/350, 380; 424/1.69; 435/7.1

(56) References Cited

U.S. PATENT DOCUMENTS 5,679,320 A  10/1997  Jacob et al. ................ 424/1.69

FOREIGN PATENT DOCUMENTS

| EP | 0 358 160 A2 | 3/1990 |
| WO | WO 89/00051 | 1/1989 |
| WO | WO 94/04702 | 3/1994 |
| WO | WO 96/01653 | 1/1996 |

OTHER PUBLICATIONS

Database Chemabs [Online] Chemical Abstracts Service, Columbus, Ohio, U.S. Udvardy, M. Et al: "RDGFAP:platelet aggregation inhibitory and profibrinolytic hybrid peptid (RGDF coupled with the carboxy terminal part of alpha.2–antiplasmin) enhances plasminogen binding to platelets" retrieved from STN Database accession No. 123:218018 XP002124573 abstract & Blood Coagulation Fibrinolysis (1995), 6(5), 481–5.

Butte et al., "A2–Antiplasmin Causes Thrombi to Resist Fibrinolysis Induced by Tissue Plasminogen Activator in Experimental Pulmonary Embolism", Circulation, vol. 95, No. 7, Apr. 1, 1997.

Lincoff et al., "Significance of a Coronary Artery With thrombolysis in Myocardial Infarction Grade 2 Flow Patency . . . ", The American Journal of Cardiology, vol. 75, May 1, 1995.

Karagounis et al., "Does Thrombolysis in Myocardial Infarction (TIMI) Perfusion Grade 2 Represent a Mostly Patent or a Mostly . . . ", JACC vol. 19, No. 1, Jan. 1992:1–10.

Salzman et al., "The epidemiology, pathogenesis and natural history of venous thrombosis, in Hemostasis . . . ", Basic Principles and Clinical Practice, 3rd ed., Philadelphia, PA, Lippincott, pp 1275–1296.

Goldhaber et al., "Randomized Controlled Trial of Tissue Plasminogen Activator in Proximal Deep Venous . . . ", 1990, Am J. Med. 88:235–240.

A Natural Cooperative Study, Circulation, Apr. 1973;47(2 Supp):II1–108, "The urokinase pulmonary embolism trial."

Goldhaber et al., "Acute Pulmonary Embolism Treated With Tissue Plasminogen Activator", 986, Lancet 2:886–889.

Rampling et al., "The Sulphite Precipitation Method for Fibrinogen Measurement; Its Use on Small . . . ", 1976, Clin. Chim. Acta. 67:43–52.

Ichinose et al., Factor XIII–mediated cross–linking of NH2–terminal peptide of a2–plasmin inhibitor to fibrin, 1983, FEBS Letters 153:369–371.

Okada et al., "Effects of Fibrin and $a_2$–Antiplasmin on Plasminogen Activation by Staphylokinase", American Journal of Hematology 53:151–157 (1996).

Schaefer et al., "$a_2$–Antiplasmin and plasminogen activator inhibitors in healing human skin wounds", Arch Dermatol Res (1996) 288:122–128.

Reed G., "Functional Characterization of Monoclonal Antibody Inhibitors of $a_2$–Antiplasmin that Accelerate . . . ", Hybridoma, vol. 16, No. 3, pp. 281–286 (1997).

Colucci et al, "In Vitro Clot Lysis as a Potential Indicator of Thrombus Resistance to Fibrinolysis . . . ", Thrombosis and Haemostasis, vol. 77 No. 4 pp. 610–807, Apr. 1997.

Duboscq et al., "Plasminogen: An Important Hemostatic Parameter in Septic Patients", Throm. Haemost. 1997; 77:1090–5.

Udvardy, M. et al. (1995) "Platelet Aggregation Inhibitory and Profibrinolytic Hybrid Peptid (RGDF coupled with the Carboxy Terminal Part of Alpha.2–antiplasmin) Enhances Plasminogen Binding To Platelets" Abstract XP002124573.

Udvardy, M. et al: RGDFAP: platelet aggregation inhibitory and profibrinolytic hybrid peptid (RDGF coupled with the carboxy terminal part of.alpha.2–antiplasmin) enhances plasminogen binding to platelets Blood Coagulation Fibrinolysis (1995), 6(5), 481–5 (abstract only).

*Primary Examiner*—Karen Cochrane Carlson
*Assistant Examiner*—Sheridan Snedden
(74) *Attorney, Agent, or Firm*—Ingrid A. Beattie; Mintz, Levin, Cohn, Ferris, Glovsky and Popeo, P.C.

(57) ABSTRACT

The invention provides methods of detecting blood in vivo and methods of inhibiting clot formation and promoting therapeutic thrombolysis using alpha-2 antiplasmin (α2AP) polypeptides.

8 Claims, 2 Drawing Sheets

| | |  | |
|---|---|---|---|
| Peptide - α2AP$_{13-24}$ | H-NQEQVSPLTLLK(Biotinyl)-OH | (SEQ ID NO:2) | |
| α2AP$_{1-24}$ - | H-MEPLGWQLTSGPNQEQVSPLTLLK-OH | (SEQ ID NO:16) | |
| 1 - | H-------A-----------------OH | (SEQ ID NO:11) | |
| 2 - | H--------------A----------OH | (SEQ ID NO:12) | |
| 3 - | H-----------------A-------OH | (SEQ ID NO:13) | |
| 4 - | H------------------N------OH | (SEQ ID NO:14) | |
| 5 - | H----------------------N---OH | (SEQ ID NO:15) | |

SEQUENCE LISTING

<160> NUMBER OF SEQ ID NOS: 17

<210> SEQ ID NO 1
<211> LENGTH: 12
<212> TYPE: PRT
<213> ORGANISM: Artificial Sequence

```
<220> FEATURE:
<221> NAME/KEY: VARIANT
<222> LOCATION: (1)...(1)
<223> OTHER INFORMATION: Xaa = Asn or Ala
<220> FEATURE:
<221> NAME/KEY: VARIANT
<222> LOCATION: (4)...(4)
<223> OTHER INFORMATION: Xaa = Gln or Lys
<220> FEATURE:
<221> NAME/KEY: VARIANT
<222> LOCATION: (5)...(5)
<223> OTHER INFORMATION: Xaa = Val or Leu
<220> FEATURE:
<221> NAME/KEY: VARIANT
<222> LOCATION: (6)...(6)
<223> OTHER INFORMATION: Xaa = Pro or Ser
<220> FEATURE:
<221> NAME/KEY: VARIANT
<222> LOCATION: (9)...(9)
<223> OTHER INFORMATION: Xaa = Thr, Ser or Ala
<223> OTHER INFORMATION: Synthetically generated

<400> SEQUENCE: 1

Xaa Gln Glx Xaa Xaa Xaa Pro Leu Xaa Leu Leu Lys
 1               5                  10

<210> SEQ ID NO 2
<211> LENGTH: 12
<212> TYPE: PRT
<213> ORGANISM: Homo sapiens

<400> SEQUENCE: 2

Asn Gln Glu Gln Val Ser Pro Leu Thr Leu Leu Lys
 1               5                  10

<210> SEQ ID NO 3
<211> LENGTH: 73
<212> TYPE: PRT
<213> ORGANISM: Homo sapiens
<220> FEATURE:
<221> NAME/KEY: VARIANT
<222> LOCATION: (1)...(73)
<223> OTHER INFORMATION: Xaa = Any Amino Acid

<400> SEQUENCE: 3

Met Glu Pro Leu Gly Xaa Gln Leu Thr Ser Gly Pro Asn Gln Glu Gln
 1               5                  10                  15

Val Ser Pro Leu Thr Leu Leu Lys Leu Gly Asn Gln Glu Pro Gly Gly
             20                  25                  30

Gln Thr Ala Leu Lys Ser Pro Gly Val Cys Ser Arg Asp Pro Thr
         35                  40                  45

Pro Glu Gln Thr His Arg Leu Ala Arg Ala Met Met Ala Phe Thr Ala
     50                  55                  60

Asp Leu Phe Ser Leu Val Ala Gln Thr
 65                  70

<210> SEQ ID NO 4
<211> LENGTH: 73
<212> TYPE: PRT
<213> ORGANISM: Homo sapiens

<400> SEQUENCE: 4

Met Glu Pro Leu Gly Trp Gln Leu Thr Ser Gly Pro Asn Gln Glu Gln
 1               5                  10                  15

Val Ser Pro Leu Thr Leu Leu Lys Leu Gly Asn Gln Glu Pro Gly Gly
             20                  25                  30
```

-continued

Gln Thr Ala Leu Lys Ser Pro Pro Gly Val Cys Ser Arg Asp Pro Thr
           35                  40                  45

Pro Glu Gln Thr His Arg Leu Ala Arg Ala Met Met Ala Phe Thr Ala
       50                  55                  60

Asp Leu Phe Ser Leu Val Ala Gln Thr
65                  70

<210> SEQ ID NO 5
<211> LENGTH: 73
<212> TYPE: PRT
<213> ORGANISM: Homo sapiens

<400> SEQUENCE: 5

Met Glu Pro Leu Gly Arg Gln Leu Thr Ser Gly Pro Asn Gln Glu Gln
1               5                  10                  15

Val Ser Pro Leu Thr Leu Leu Lys Leu Gly Asn Gln Glu Pro Gly Gly
                20                  25                  30

Gln Thr Ala Leu Lys Ser Pro Pro Gly Val Cys Ser Arg Asp Pro Thr
           35                  40                  45

Pro Glu Gln Thr His Arg Leu Ala Arg Ala Met Met Ala Phe Thr Ala
       50                  55                  60

Asp Leu Phe Ser Leu Val Ala Gln Thr
65                  70

<210> SEQ ID NO 6
<211> LENGTH: 73
<212> TYPE: PRT
<213> ORGANISM: Homo sapiens

<400> SEQUENCE: 6

Met Glu Pro Leu Asp Leu Gln Leu Met Asp Gly Gln Ala Gly Gln Lys
1               5                  10                  15

Leu Pro Pro Leu Ser Leu Leu Lys Leu Asp Asn Gln Glu Pro Gly Gly
                20                  25                  30

Gln Ile Ala Pro Lys Lys Ala Pro Glu Asp Cys Lys Leu Ser Pro Thr
           35                  40                  45

Pro Glu Gln Thr Arg Arg Leu Ala Arg Ala Met Met Thr Phe Thr Thr
       50                  55                  60

Asp Leu Phe Ser Leu Val Ala Gln Ser
65                  70

<210> SEQ ID NO 7
<211> LENGTH: 73
<212> TYPE: PRT
<213> ORGANISM: Homo sapiens

<400> SEQUENCE: 7

Val Asp Leu Pro Gly Gln Gln Pro Val Ser Glu Gln Ala Gln Gln Lys
1               5                  10                  15

Leu Pro Leu Pro Ala Leu Phe Lys Leu Asp Asn Gln Asp Phe Gly Asp
                20                  25                  30

His Ala Thr Leu Lys Arg Ser Pro Gly His Cys Lys Ser Val Pro Thr
           35                  40                  45

Ala Glu Glu Thr Arg Arg Leu Ala Gln Ala Met Met Ala Phe Thr Thr
       50                  55                  60

Asp Leu Phe Ser Leu Val Ala Gln Thr
65                  70

-continued

```
<210> SEQ ID NO 8
<211> LENGTH: 488
<212> TYPE: PRT
<213> ORGANISM: Homo sapiens

<400> SEQUENCE: 8

Leu Trp Gly Leu Leu Val Leu Ser Trp Ser Cys Leu Gln Gly Pro Cys
  1               5                  10                  15

Ser Val Phe Ser Pro Val Ser Ala Met Glu Pro Leu Gly Arg Gln Leu
             20                  25                  30

Thr Ser Gly Pro Asn Gln Glu Gln Val Ser Pro Leu Thr Leu Leu Lys
         35                  40                  45

Leu Gly Asn Gln Glu Pro Gly Gly Gln Thr Ala Leu Lys Ser Pro Pro
     50                  55                  60

Gly Val Cys Ser Arg Asp Pro Thr Pro Glu Gln Thr His Arg Leu Ala
 65                  70                  75                  80

Arg Ala Met Met Ala Phe Thr Ala Asp Leu Phe Ser Leu Val Ala Gln
                 85                  90                  95

Thr Ser Thr Cys Pro Asn Leu Ile Leu Ser Pro Leu Ser Val Ala Leu
            100                 105                 110

Ala Leu Ser His Leu Ala Leu Gly Ala Gln Asn His Thr Leu Gln Arg
        115                 120                 125

Leu Gln Gln Val Leu His Ala Gly Ser Gly Pro Cys Leu Pro His Leu
    130                 135                 140

Leu Ser Arg Leu Cys Gln Asp Leu Gly Pro Gly Ala Phe Arg Leu Ala
145                 150                 155                 160

Ala Arg Met Tyr Leu Gln Lys Gly Phe Pro Ile Lys Glu Asp Phe Leu
                165                 170                 175

Glu Gln Ser Glu Gln Leu Phe Gly Ala Lys Pro Val Ser Leu Thr Gly
            180                 185                 190

Lys Gln Glu Asp Asp Leu Ala Asn Ile Asn Gln Trp Val Lys Glu Ala
        195                 200                 205

Thr Glu Gly Lys Ile Gln Glu Phe Leu Ser Gly Leu Pro Glu Asp Thr
    210                 215                 220

Val Leu Leu Leu Leu Asn Ala Ile His Phe Gln Gly Phe Trp Arg Asn
225                 230                 235                 240

Lys Phe Asp Pro Ser Leu Thr Gln Arg Asp Ser Phe His Leu Asp Glu
                245                 250                 255

Gln Phe Thr Val Pro Val Glu Met Met Gln Ala Arg Thr Tyr Pro Leu
            260                 265                 270

Arg Trp Phe Leu Leu Glu Gln Pro Glu Ile Gln Val Ala Asp Phe Pro
        275                 280                 285

Phe Lys Asn Asn Met Ser Phe Val Val Leu Val Pro Thr His Phe Glu
    290                 295                 300

Trp Asn Val Ser Gln Val Leu Ala Asn Leu Ser Trp Asp Thr Leu His
305                 310                 315                 320

Pro Pro Leu Val Trp Glu Arg Pro Thr Lys Val Arg Leu Pro Lys Leu
                325                 330                 335

Tyr Leu Lys His Gln Met Asp Leu Val Ala Thr Leu Ser Gln Leu Gly
            340                 345                 350

Leu Gln Glu Leu Phe Gln Ala Pro Asp Leu Arg Gly Ile Ser Glu Gln
        355                 360                 365

Ser Leu Val Val Ser Gly Val Gln His Gln Ser Thr Leu Glu Leu Ser
    370                 375                 380
```

```
Glu Val Gly Val Glu Ala Ala Ala Thr Ser Ile Ala Met Ser Arg
385                 390                 395                 400

Met Ser Leu Ser Ser Phe Ser Val Asn Arg Pro Phe Leu Phe Ile
            405                 410                 415

Phe Glu Asp Thr Thr Gly Leu Pro Leu Phe Val Gly Ser Val Arg Asn
                420                 425                 430

Pro Asn Pro Ser Ala Pro Arg Glu Leu Lys Glu Gln Gln Asp Ser Pro
            435                 440                 445

Gly Asn Lys Asp Phe Leu Gln Ser Leu Lys Gly Phe Pro Arg Gly Asp
            450                 455                 460

Lys Leu Phe Gly Pro Asp Leu Lys Leu Val Pro Pro Met Glu Glu Asp
465                 470                 475                 480

Tyr Pro Gln Phe Gly Ser Pro Lys
                485

<210> SEQ ID NO 9
<211> LENGTH: 492
<212> TYPE: PRT
<213> ORGANISM: Bovine

<400> SEQUENCE: 9

Met Ala Leu Leu Trp Gly Leu Leu Val Leu Ser Trp Ser Cys Leu Gln
1               5                   10                  15

Gly Pro Cys Ser Val Phe Ser Pro Val Ser Ala Met Glu Pro Leu Gly
                20                  25                  30

Arg Gln Leu Thr Ser Gly Pro Asn Gln Glu Gln Val Ser Pro Leu Thr
            35                  40                  45

Leu Leu Lys Leu Gly Asn Gln Glu Pro Gly Gly Gln Thr Ala Leu Lys
    50                  55                  60

Ser Pro Pro Gly Val Cys Ser Arg Asp Pro Thr Pro Glu Gln Thr His
65                  70                  75                  80

Arg Leu Ala Arg Ala Met Met Ala Phe Thr Ala Asp Leu Phe Ser Leu
                85                  90                  95

Val Ala Gln Thr Ser Thr Cys Pro Asn Leu Ile Leu Ser Pro Leu Ser
                100                 105                 110

Val Ala Leu Ala Leu Ser His Leu Ala Leu Gly Ala Gln Asn His Thr
            115                 120                 125

Leu Gln Arg Leu Gln Gln Val Leu His Ala Gly Ser Gly Pro Cys Leu
    130                 135                 140

Pro His Leu Leu Ser Arg Leu Cys Gln Asp Leu Gly Pro Gly Ala Phe
145                 150                 155                 160

Arg Leu Ala Ala Arg Met Tyr Leu Gln Lys Gly Phe Pro Ile Lys Glu
                165                 170                 175

Asp Phe Leu Glu Gln Ser Glu Gln Leu Phe Gly Ala Lys Pro Val Ser
            180                 185                 190

Leu Thr Gly Lys Gln Glu Asp Asp Leu Ala Asn Ile Asn Gln Trp Val
    195                 200                 205

Lys Glu Ala Thr Glu Gly Lys Ile Gln Glu Phe Leu Ser Gly Leu Pro
210                 215                 220

Glu Asp Thr Val Leu Leu Leu Asn Ala Ile His Phe Gln Gly Phe
225                 230                 235                 240

Trp Arg Asn Lys Phe Asp Pro Ser Leu Thr Gln Arg Asp Ser Phe His
                245                 250                 255

Leu Asp Glu Gln Phe Thr Val Pro Val Glu Met Met Gln Ala Arg Thr
            260                 265                 270
```

-continued

Tyr Pro Leu Arg Trp Phe Leu Leu Glu Gln Pro Glu Ile Gln Val Ala
             275                 280                 285
His Phe Pro Phe Lys Asn Asn Met Ser Phe Val Val Leu Val Pro Thr
290                 295                 300
His Phe Glu Trp Asn Val Ser Gln Val Leu Ala Asn Leu Ser Trp Asp
305                 310                 315                 320
Thr Leu His Pro Pro Leu Val Trp Glu Arg Pro Thr Lys Val Arg Leu
                 325                 330                 335
Pro Lys Leu Tyr Leu Lys His Gln Met Asp Leu Val Ala Thr Leu Ser
             340                 345                 350
Gln Leu Gly Leu Gln Glu Leu Phe Gln Ala Pro Asp Leu Arg Gly Ile
             355                 360                 365
Ser Glu Gln Ser Leu Val Val Ser Gly Val Gln His Gln Ser Thr Leu
370                 375                 380
Glu Leu Ser Glu Val Gly Val Glu Ala Ala Ala Thr Ser Ile Ala
385                 390                 395                 400
Met Ser Arg Met Ser Leu Ser Ser Phe Ser Val Asn Arg Pro Phe Leu
                 405                 410                 415
Phe Phe Ile Phe Glu Asp Thr Thr Gly Leu Pro Leu Phe Val Gly Ser
             420                 425                 430
Val Arg Asn Pro Asn Pro Ser Ala Pro Arg Glu Leu Lys Glu Gln Gln
             435                 440                 445
Asp Ser Pro Gly Asn Lys Asp Phe Leu Gln Ser Leu Lys Gly Phe Pro
             450                 455                 460
Arg Gly Asp Lys Leu Phe Gly Pro Asp Leu Lys Leu Val Pro Pro Met
465                 470                 475                 480
Glu Glu Asp Tyr Pro Gln Phe Gly Ser Pro Lys Leu
                 485                 490

<210> SEQ ID NO 10
<211> LENGTH: 491
<212> TYPE: PRT
<213> ORGANISM: Homo sapiens

<400> SEQUENCE: 10

Met Ala Leu Leu Arg Gly Leu Leu Val Leu Ser Leu Ser Cys Leu Gln
1                 5                  10                  15
Gly Pro Cys Phe Thr Phe Ser Pro Val Ser Ala Val Asp Leu Pro Gly
                 20                  25                  30
Gln Gln Pro Val Ser Glu Gln Ala Gln Gln Lys Leu Pro Leu Pro Ala
             35                  40                  45
Leu Phe Lys Leu Asp Asn Gln Asp Phe Gly Asp His Ala Thr Leu Lys
     50                  55                  60
Arg Ser Pro Gly His Cys Lys Ser Val Pro Thr Ala Glu Glu Thr Arg
65                  70                  75                  80
Arg Leu Ala Gln Ala Met Met Ala Phe Thr Thr Asp Leu Phe Ser Leu
                 85                  90                  95
Val Ala Gln Thr Ser Thr Ser Ser Asn Leu Val Leu Ser Pro Leu Ser
                 100                 105                 110
Val Ala Leu Ala Leu Ser His Leu Ala Leu Gly Ala Gln Asn Gln Thr
             115                 120                 125
Leu His Ser Leu His Arg Val Leu His Met Asn Thr Gly Ser Cys Leu
     130                 135                 140
Pro His Leu Leu Ser His Phe Tyr Gln Asn Leu Gly Pro Gly Thr Ile

-continued

```
                145                 150                 155                 160
Arg Leu Ala Ala Arg Ile Tyr Leu Gln Lys Gly Phe Pro Ile Lys Asp
                    165                 170                 175

Asp Phe Leu Glu Gln Ser Glu Arg Leu Phe Gly Ala Lys Pro Val Lys
            180                 185                 190

Leu Thr Gly Lys Gln Glu Glu Asp Leu Ala Asn Ile Asn Gln Trp Val
        195                 200                 205

Lys Glu Ala Thr Glu Gly Lys Ile Glu Asp Phe Leu Ser Glu Leu Pro
    210                 215                 220

Asp Ser Thr Val Leu Leu Leu Asn Ala Ile His Phe His Gly Phe
225                 230                 235                 240

Trp Arg Thr Lys Phe Asp Pro Ser Leu Thr Gln Lys Asp Phe His
                245                 250                 255

Leu Asp Glu Arg Phe Thr Val Ser Val Asp Met Met His Ala Val Ser
                260                 265                 270

Tyr Pro Leu Arg Trp Phe Leu Glu Gln Pro Glu Ile Gln Val Ala
                275                 280                 285

His Phe Pro Phe Lys Asn Asn Met Ser Phe Val Val Met Pro Thr
    290                 295                 300

Tyr Phe Glu Trp Asn Val Ser Glu Val Leu Ala Asn Leu Thr Trp Asp
305                 310                 315                 320

Thr Leu Tyr His Pro Ser Leu Gln Glu Arg Pro Thr Lys Val Trp Leu
                325                 330                 335

Pro Lys Leu His Leu Gln Gln Leu Asp Leu Val Ala Thr Leu Ser
                340                 345                 350

Gln Leu Gly Leu Gln Glu Leu Phe Gln Gly Pro Asp Leu Arg Gly Ile
        355                 360                 365

Ser Glu Gln Asn Leu Val Val Ser Ser Val Gln His Gln Ser Thr Met
    370                 375                 380

Glu Leu Ser Glu Ala Gly Val Glu Ala Ala Ala Thr Ser Val Ala
385                 390                 395                 400

Met Asn Arg Met Ser Leu Ser Ser Phe Thr Val Asn Arg Pro Phe Leu
                405                 410                 415

Phe Phe Ile Met Glu Asp Thr Ile Gly Val Pro Leu Phe Val Gly Ser
                420                 425                 430

Val Arg Asn Pro Asn Pro Ser Ala Leu Pro Gln Leu Gln Glu Gln Arg
            435                 440                 445

Asp Ser Pro Asp Asn Arg Leu Ile Gly Gln Asn Asp Lys Ala Asp Phe
    450                 455                 460

His Gly Gly Lys Thr Phe Gly Pro Asp Leu Lys Leu Ala Pro Arg Met
465                 470                 475                 480

Glu Glu Asp Tyr Pro Gln Phe Ser Ser Pro Lys
                485                 490

<210> SEQ ID NO 11
<211> LENGTH: 24
<212> TYPE: PRT
<213> ORGANISM: Homo sapiens

<400> SEQUENCE: 11

Met Glu Pro Leu Gly Trp Ala Leu Thr Ser Gly Pro Asn Gln Glu Gln
  1                 5                  10                  15

Val Ser Pro Leu Thr Leu Leu Lys
                20
```

-continued

<210> SEQ ID NO 12
<211> LENGTH: 24
<212> TYPE: PRT
<213> ORGANISM: Homo sapiens

<400> SEQUENCE: 12

Met Glu Pro Leu Gly Trp Gln Leu Thr Ser Gly Pro Asn Ala Glu Gln
1               5                   10                  15

Val Ser Pro Leu Thr Leu Leu Lys
            20

<210> SEQ ID NO 13
<211> LENGTH: 24
<212> TYPE: PRT
<213> ORGANISM: Homo sapiens

<400> SEQUENCE: 13

Met Glu Pro Leu Gly Trp Gln Leu Thr Ser Gly Pro Asn Gln Glu Ala
1               5                   10                  15

Val Ser Pro Leu Thr Leu Leu Lys
            20

<210> SEQ ID NO 14
<211> LENGTH: 24
<212> TYPE: PRT
<213> ORGANISM: Homo sapiens

<400> SEQUENCE: 14

Met Glu Pro Leu Gly Trp Gln Leu Thr Ser Gly Pro Asn Gln Glu Gln
1               5                   10                  15

Asn Ser Pro Leu Thr Leu Leu Lys
            20

<210> SEQ ID NO 15
<211> LENGTH: 24
<212> TYPE: PRT
<213> ORGANISM: Homo sapiens

<400> SEQUENCE: 15

Met Glu Pro Leu Gly Trp Gln Leu Thr Ser Gly Pro Asn Gln Glu Gln
1               5                   10                  15

Val Ser Pro Leu Thr Asn Leu Lys
            20

<210> SEQ ID NO 16
<211> LENGTH: 24
<212> TYPE: PRT
<213> ORGANISM: Homo sapiens

<400> SEQUENCE: 16

Met Glu Pro Leu Gly Trp Gln Leu Thr Ser Gly Pro Asn Gln Glu Gln
1               5                   10                  15

Val Ser Pro Leu Thr Leu Leu Lys
            20

<210> SEQ ID NO 17
<211> LENGTH: 24
<212> TYPE: PRT
<213> ORGANISM: Homo sapiens

<400> SEQUENCE: 17

Met Glu Pro Leu Gly Trp Gln Leu Thr Ser Gly Pro Asn Gln Ala Gln

-continued

```
            1               5              10              15
Val Ser Pro Leu Thr Leu Leu Lys
                        20
```

METHODS OF INHIBITING CLOT FORMATION

This application claims priority to provisional application No. 60/087,218, filed May 29, 1998.

STATEMENT AS TO FEDERALLY SPONSORED RESEARCH

This invention was made with government support under National Institutes of Health grant HL-57314. The U.S. government has certain rights in the invention.

BACKGROUND OF THE INVENTION

This invention relates to inhibition and detection of blood clot formation.

The resistance of thrombi to fibrinolysis induced by plasminogen activators is an impediment to the successful treatment of thrombotic diseases. Fibrinolytic resistance is evident in patients with acute thrombotic coronary occlusion, where treatment with plasminogen activators results in full coronary reperfusion in only 33–55% of patients at 90 minutes (Lincoff et al., 1995, Am. J. Cardiol. 75:871–876; Karagounis et al., 1992, J. Am. Coll. Cardiol. 19:1–10). The resistance of thrombi to lysis by plasminogen activators may be even more marked in patients with venous thromboembolism. In deep venous thrombosis treated with tissue plasminogen activator (TPA), nearly two thirds of patients have minimal or no significant lysis evident on repeat venography at 24 hours (Salzman et al., 1994, The epidemiology, pathogenesis and natural history of venous thrombosis, in Hemostasis and Thrombosis: Basic Principles and Clinical Practice, 3rd ed., Philadelphia, Pa.: Lippincott, pp 1275–1296; Goldhaber et al., 1990, Am. J. Med. 88:235–240). In patients with pulmonary embolism, TPA restores blood flow within 24 hours to only about a third of occluded lung segments, as judged by serial perfusion scanning (The Urokinase Pulmonary Embolism Trial. A national cooperative study, 1973, Circulation 47:1–108; Goldhaber et al., 1986, Lancet 2:886–889). Improved thrombolysis may reduce mortality and morbidity associated with thrombotic disease.

SUMMARY OF THE INVENTION

The invention provides methods of improving therapeutic thrombolysis, detecting blood clots in vivo, and inhibiting clot formation using alpha-2 antiplasmin (α2AP) polypeptides.

To detect blood clot formation in a mammal, a diagnostically effective amount of a detectably labeled alpha-2 antiplasmin (α2AP) polypeptide is administered to the mammal, and association of the polypeptide with a blood clot determined. Association of the α2AP polypeptide with a vascular obstruction, e.g, via α2AP-fibrin crosslinking, is an indication of the presence blood clot formation at the site of the obstruction. Since α2AP crosslinks with fibrin in actively forming blood clots but not at the site of old (i.e., not actively forming) blood clots, the method is useful to characterize blood vessel obstructions as pre-existing or actively forming. Newly forming thrombi are detected by virtue of the formation of α2AP polypeptide-fibrin crosslinks mediated by activated factor XIIIa. Thus, the present method provides an advantage over conventional visual detection techniques such as scintiphotography and angiography with which such characterization is difficult or unachievable.

The polypeptides of the invention are substantially pure. Polypeptides or other compounds encompassed by the invention are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

The α2AP polypeptide preferably contains the amino acid sequence of $X_1QX_2X_3X_4X_5PLX_6LLK$ (SEQ ID NO:1), wherein $X_1$=N or A, $X_2$=E or Q, $X_3$=Q or K, $X_4$=V or L, $X_5$=P or S, and $X_6$=T, S or A (the Q residue indicated in bold type is involved if α2AP-fibrin crosslinking). For example, the polypeptide comprises the amino acid sequence of α2AP$_{13\text{-}24}$ NQEQVSPLTLLK (SEQ ID NO:2) or α2AP$_{1\text{-}24}$ (MEPLGWQLTSGPNQEQVSPLTLLK; SEQ ID NO:16). Polypeptides derived from human α2AP-include those which contain a sequence that is 80–100% identical to the amino acid sequence of MEPLGXQLTS GPNQEQVSPL TLLKLGNQEP GGQTALKSPP GVCSRDPTPE QTHRLARAMM AFTADLFSLV AQT (SEQ ID NO:3), where "X" represents a residue that can differ among human α2AP variants. Human N-terminal α2AP polypeptides include those which contain the amino acid sequence MEPLGWQLTS GPNQEQVSPL TLLKLGNQEP GGQTALKSPP GVCSRDPTPE QTHRLARAMM AFTADLFSLV AQT (SEQ ID NO:4) or MEPLGRQLTS GPNQEQVSPL TLLKLGNQEP GGQTALKSPP GVCSRDPTPE QTHRLARAMM AFTADLFSLV AQT (SEQ ID NO:5). Alternatively, the polypeptide may contain a sequence that is 80–100% identical to the amino acid MEPLDLQLMD GQAQQKLPPL SLLKLDNQEP GGQIAPKKAP EDCKLSPTPE QTRRLARAMM TFTTDLFSLV AQS (SEQ ID NO:6), corresponding to an N-terminal fragment of naturally-occurring bovine α2AP, or VDLPGQQPVS EQAQQKLPLP ALFKLDNQDF GDHATLKRSP GHCKSVPTAE ETRRLAQAMM AFTTDLFSLV AQT (SEQ ID NO:7), corresponding to an N-terminal fragment of naturally-occurring mouse α2AP. An α2AP polypeptide is a peptide with at least 80–100% sequence identity to a portion of a naturally-occurring α2AP protein but having a length that is shorter than the length of the naturally-occurring mature full-length α2AP protein. Human α2AP variants within the invention include those with the amino acid sequence of SEQ ID NO:11, 13, 15, or 17.

The invention also features methods of preventing the development of clots in patients at risk for thrombosis and methods of treating patients with thrombotic conditions such as stroke, myocardial infarction, pulmonary embolism, and deep venous thrombosis. For example, a method of inhibiting blood clot formation in a mammal is carried out by administering to the mammal a therapeutically effective amount of an α2AP polypeptide. A method of preventing and lysing blood clots is carried out by co-administering to a mammal a therapeutically effective amount of an α2AP polypeptide and a thrombolytic agent such as a plasminogen activator, e.g., tissue plasminogen activator (t-PA). Thrombolytic agents such as prourokinase, urokinase, streptokinase, staphylokinase, and vampire bat-derived plasminogen activator may be co-administered with an α2AP polypeptide to increase the effectiveness of the thrombolytic agent.

α2AP polypeptides and peptide mimetics thereof are useful in the diagnostic and therapeutic methods described above. Preferably the α2AP polypeptide is derived from the N-terminus of a mature, naturally-occurring mammalian α2AP protein. For example, the polypeptides may be derived from human, bovine, or mouse α2AP proteins, the amino acid sequences of which are shown in Tables 1–3, respectively (the first amino acid of the mature protein is indicated with an arrow).

TABLE 1

HUMAN α2AP

```
                             →
  1 LWGLLVLSWS CLQGPCSVFS PVSAMEPLGR QLTSGPNQEQ VSPLTLLKLG NQEPGGQTAL
 61 KSPPGVCSRD PTPEQTHRLA RAMMAFTADL FSLVAQTSTC PNLILSPLSV ALALSHLALG
121 AQNHTLQRLQ QVLHAGSGPC LPHLLSRLCQ DLGPGAFRLA ARMYLQKGFP IKEDFLEQSE
181 QLFGAKPVSL TGKQEDDLAN INQWVKEATE GKIQEFLSGL PEDTVLLLLN AIHFQGFWRN
241 KFDPSLTQRD SFHLDEQFTV PVEMMQARTY PLRWFLLEQP EIQVADFPFK NNMSFVVLVP
301 THFEWNVSQV LANLSWDTLH PPLVWERPTK VRLPKLYLKH QMDLVATLSQ LGLQELFQAP
361 DLRGISEQSL VVSGVQHQST LELSEVGVEA AAATSIAMSR MSLSSFSVNR PFLFFIFEDT
421 TGLPLFVGSV RNPNPSAPRE LKEQQDSPGN KDFLQSLKGF PRGDKLFGPD LKLVPPMEED
481 YPQFGSPK (SEQ ID NO:8)
```

TABLE 2

BOVINE α2AP

```
                                 →
  1 MALLWGLLVL SWSCLQGPCS VFSPVSAMEP LGRQLTSGPN QEQVSPLTLL KLGNQEPGGQ
 61 TALKSPPGVC SRDPTPEQTH RLARAMMAFT ADLFSLVAQT STCPNLILSP LSVALALSHL
121 ALGAQNHTLQ RLQQVLHAGS GPCLPHLLSR LCQDLGPGAF RLAARMYLQK GFPIKEDFLE
181 QSEQLFGAKP VSLTGKQEDD LANINQWVKE ATEGKIQEFL SGLPEDTVLL LLNAIHFQGF
241 WRNKFDPSLT QRDSFHLDEQ FTVPVEMMQA RTYPLRWFLL EQPEIQVAHF PFKNNMSFVV
301 LVPTHFEWNV SQVLANLSWD TLHPPLVWER PTKVRLPKLY LKHQMDLVAT LSQLGLQELF
361 QAPDLRGISE QSLVVSGVQH QSTLELSEVG VEAAAATSIA MSRMSLSSFS VNRPFLFFIF
421 EDTTGLPLFV GSVRNPNPSA PRELKEQQDS PGNKDFLQSL KGFPRGDKLF GPDLKLVPPM
481 EEDYPQFGSP K  (SEQ ID NO:9)
```

TABLE 3

MOUSE α2AP

```
  1 MALLRGLLVL SLSCLQGPCF TFSPVSAVDL PGQQPVSEQA QQKLPLPALF KLDNQDFGDH
 61 ATLKRSPGHC KSVPTAEETR RLAQAMMAFT TDLFSLVAQT STSSNLVLSP LSVALALSHL
121 ALGAQNQTLH SLHRVLHMNT GSCLPHLLSH FYQNLGPGTI RLAARIYLQK GFPIKDDFLE
181 QSERLFGAKP VKLTGKQEED LANINQWVKE ATEGKIEDFL SELPDSTVLL LLNAIHFHGF
241 WRTKFDPSLT QKDFFHLDER FTVSVDMMHA VSYPLRWFLL EQPEIQVAHF PFKNNMSFVV
301 VMPTYFEWNV SEVLANLTWD TLYHPSLQER PTKVWLPKLH LQQQLDLVAT LSQLGLQELF
361 QGPDLRGISE QNLVVSSVQH QSTMELSEAG VEAAAATSVA MNRMSLSSFT VNRPFLFFIM
421 EDTIGVPLFV GSVRNPNPSA LPQLQEQRDS PDNRLIGQND KADFHGGKTF GPDLKLAPRM
481 EEDYPQFSSP K  (SEQ ID NO:10)
```

The length of an α2AP polypeptide is preferably 12 to 250 amino acids, inclusive. More preferably, the length is 10 to 75 amino acids, inclusive, e.g., a polypeptide that is 12 amino acids in length and has an amino acid sequence of NQEQVSPLTLLK (SEQ ID NO:2).

The amino acid sequence of the polypeptide preferably contains the amino acid sequence of $X_1QX_2X_3X_4X_5PLX_6LLK$ (SEQ ID NO:1), wherein $X_1$=N or A, $X_2$=E or Q, $X_3$=Q or K, $X_4$=V or L, $X_5$=P or S, and $X_6$=T, S or A. Examples of such polypeptides include those derived from human α2AP (e.g., SEQ ID NO:4 or 5) and those derived from bovine α2AP (e.g., SEQ ID NO:6). An α2AP polypeptide derived from mouse α2AP contains the amino acid sequence of SEQ ID NO:7. Shorter polypeptides such as those containing amino acids 1–24, 1–41, 10–24, and 13–24 (e.g., SEQ ID NO:2) of each of SEQ ID NO:4, 5, 6, or 7 are also useful to detect and treat thrombotic conditions.

Preferably, the α2AP polypeptide contains an amino acid sequence with 80–100% sequence identity to SEQ ID NO: 3, 4, 5, 6, or 7 in which a non-identical amino acid of the polypeptide is a conservative amino acid substitution and the polypeptide functions to inhibit α2AP-fibrin crosslinking. Sequence identity is measured using standard sequence analysis software (e.g., the Sequence Analysis Software Package of the Genetics Computer Group, University of Wisconsin Biotechnology Center, 1710 University Avenue, Madison, Wis. 53705), with the default parameters as specified therein.

Peptide mimetics of an α2AP polypeptide are also within the invention. Preferably, the length of the peptide mimetic is 12 to 250 amino acids, inclusive, and contains the amino acid sequence of SEQ ID NO:1. For example, an α2AP peptide mimetic contains an amino acid sequence with 80–100% sequence identity to SEQ ID NO: 2; the non-identical amino acids of the polypeptide are conservative amino acid substitutions; and the polypeptide inhibits α2AP-fibrin crosslinking.

For diagnostic applications, the polypeptide is detectably labeled, e.g., the polypeptide is biotinylated or tagged with a radioisotope. In addition to administering α2AP polypeptides to a mammal to prevent clot formation or promote physiologic thrombolysis or improving the effectiveness of therapeutically-induced thrombolysis, the polypeptide can be used as targeting agents to deliver therapeutic agents to the site of a actively forming blood clot. For example, any of the α2AP polypeptides or peptide mimetic are linked to a therapeutic agent (e.g., a thrombolytic agent). Such chimeric compounds are recombinantly produced or cosynthesized. Thus, the invention includes a method of targeting a therapeutic agent to an actively developing thrombus in a mammal by administering to the mammal an N-terminal α2AP polypeptide linked to a therapeutic agent.

Other features and advantages of the invention will be apparent from the following description of the preferred embodiments thereof, and from the claims.

BRIEF DESCRIPTION OF THE DRAWINGS

FIG. 1A shows the effect of factor XIIIa activity on resistance to endogenous fibrinolysis. Anesthetized ferrets were treated with heparin (100 units/kg), and radiolabeled plasma clots were embolized to the lungs. Factor XIIIa activity was normal in emboli in control animals or inhibited in the F13-I group. "F13-I" is a monoclonal antibody (9C11) which is capable of quenching all factor XIIIa-mediated crosslinking (i.e., both fibrin y-chain crosslinking and α2-antiplasmin-fibrin crosslinking are completely inhibited). Lysis was significantly higher in the F13-I group than in the control group ($p<0.0001$). FIG. 1B shows the effect of α2 antiplasmin-fibrin crosslinking and total factor XIIIa activity on resistance to pharmacologic lysis of pulmonary emboli in animals treated with TPA (1 mg/kg). Lysis of pulmonary emboli in the presence of TPA (normal factor XIIIa activity), TPA+F13-I (inhibited factor XIIIa activity), and TPA+α2AP-I (selectively inhibited α2 antiplasmin-fibrin crosslinking) is depicted. "α2AP-I" is a polypeptide with the amino acid sequence of SEQ ID NO:2; this polypeptide selectively. inhibits only factor XIIIa-mediated α2AP-fibrin crosslinking. In animals with normal factor XIIIa activity, the addition of TPA significantly increased lysis (control vs TPA; $p<0.005$). Inhibition of α2 antiplasmin-fibrin crosslinking significantly increased lysis (TPA+α2AP-I vs TPA; $p<0.0005$). Full inhibition of factor XIIIa activity caused higher lysis than that obtained in both the normal factor XIIIa group (TPA+F13-I vs TPA; $p<0.0001$), and the group in which α2 antiplasmin-fibrin crosslinking had been inhibited (TPA+F13-I vs TPA+α2AP-I; $p<0.0005$). Mean lysis (±SD) and number of animals in each experimental group are shown.

DETAILED DESCRIPTION

Figure 1A:
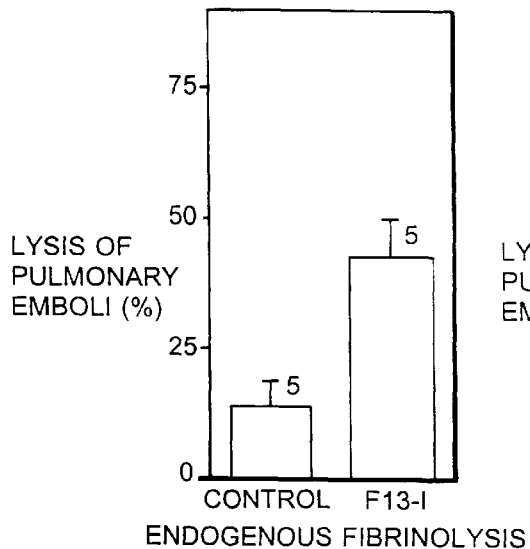
FIGS. 1A and 1B are bar graphs showing the effects of factor XIIIa-mediated crosslinking on the resistance of pulmonary emboli to endogenous and pharmacologic lysis.

α2AP polypeptides inhibit factor XIIIa-mediated crosslinking of endogenous α2AP with fibrin, thereby causing thrombi to undergo spontaneous physiologic lysis or accelerated lysis when administered with therapeutic thrombolytic agents.

Factor XIIIa catalyzes the formation of covalent bonds between glutamine and lysine residues in the γ and α chains of adjacent fibrin molecules, which markedly increase the mechanical durability of the fibrin polymer. Factor XIIIa also rapidly crosslinks α2AP, the fast acting plasmin inhibitor, to fibrin. The relative contribution of fibrin-fibrin crosslinking, or of α2 antiplasmin-fibrin crosslinking, to fibrinolytic resistance in vitro is still debated.

In vivo, human thromboemboli show evidence of extensive α2AP-fibrin crosslinking by factor XIIIa, and highly crosslinked thrombi are more resistant to lysis in vitro. The contribution of factor XIIIa-mediated fibrin-fibrin crosslinking and α2 antiplasmin-fibrin crosslinking to the fibrinolytic resistance of experimental pulmonary emboli was examined. The data described herein indicates that factor XIIIa-mediated fibrin-fibrin and α2AP-fibrin crosslinking is the underlying mechanism of resistance of pulmonary emboli to endogenous and TPA-induced fibrinolysis and that α2AP polypeptides crosslink with fibrin, thereby inhibiting crosslinking of fibrin with endogenous α2AP protein.

Reagents

Materials were obtained from the following suppliers: aprotinin, Sigma (St. Louis, Mo.); calcium chloride, Mallinckrodt (Paris, Ky.); purified factor XIII and fibrinogen, American Diagnostica (Greenwich, Conn.); goat antimouse antibody, Cappel Organon Technika (Durham, N.C.); heparin (1000 units/ml), Elkins-Sinn Inc (Cherry Hill, N.J.); fresh-frozen human plasma pooled from random donors; TPA with a specific activity of 580,000 IU/mg, Genentech (South San Francisco, Calif.); normal saline for intravenous use, Travenol Laboratories (Deerfield, Ill.); sodium iodide, Aldrich Chemical Co (Milwaukee, Wis.); NaI25I, Dupont-NEN (Cambridge, Mass.); and bovine thrombin, Parke-Davis (Morris Plains, N.J.). Microcentrifuge tubes were obtained from National Scientific Supply Co (San Rafael, Calif.).

Ferrets (weighing approximately 0.8 to 1 kg) were purchased from Marshall Farms (New York, N.Y.). Ketamine (100 mg/ml) was obtained from Fort Dodge Laboratories (Fort Dodge, Iowa) and acepromazine maleate from Fermenta Animal Health Co. (Kansas City, Mo.). The surgical instruments were purchased from VWR (Boston) and the tubing from Namic (Glens Falls, N.Y.). Bard Parker surgical blades were from Becton Dickinson (Franklin Lake, N.J.), 4.0 silk sutures from American Cyanamid Co (Danbury, Conn.), Surflo IV catheter and 20 gauge 1¼-inch Venoject tubes with K3EDTA from Terumo Medical Corp (Elkton, Md.), and sterile three-way stopcocks from Mallinckrodt Critical Care (Glens Falls, N.Y.). An auto syringe infusion pump (Baxter Health Care Corp, Hooksett, N.H.) was used with tubing and a microbore 60 inch extension set obtained from McGaw of Puerto Rico (Sabana Grand, Puerto Rico).

Anti-Factor XIII Monoclonal Antibody Production and Purification

Hybridoma cells which produce monoclonal antibody 9C11 (which is specific for the catalytic A subunit of human factor XIII) is available from the American Type Culture Collection (ATCC Designation No. CRL 11458). The hybridoma producing 9C11 was cloned by limiting dilution and expanded into ascites in pristane-primed Balb/C mice. Antibody was purified from filtered ascites by precipitation with 40% ammonium sulfate. After resuspension and dialysis into 10 mM $KH_2PO_4$, pH 7.2, proteins were absorbed on a DEAE-Affigel Blue Sepharose column and monoclonal antibody 9C11 was eluted with a linear gradient spanning 0 to 100 mM NaCl. Eluted protein was collected in fractions and analyzed by SDS-polyacrylamide electrophoresis on 10% gels.

Inhibition of Fibrin-Fibrin Crosslinking and α2 Antiplasmin-Fibrin Crosslinking in vitro To determine the dose of factor XIII inhibitor or α2AP polypeptide required to inhibit factor XIII-mediated crosslinking, various concentrations of anti-factor XIII antibody 9C11 (10 μl; 0–10 μg) was mixed with fresh-frozen plasma (45 μl), bovine thrombin (100 units/ml; 3 μl), and calcium chloride (0.4 M; 2.5 μl). After clotting for 90 minutes at 37° C., the clots were compressed and washed three times in 500 μl of saline to remove unbound protein. The clots were solubilized in 95 μl of 9 M urea and 5 μl of β-mercaptoethanol at 37° C. for 30 min. Clots were then mixed in 100 μl of SDS sample buffer with 20 μl of bromphenol blue-glycerol solution and incubated at 85° C. for 5 min. Proteins were electrophoresed on 6% SDS-polyacrylamide gels and electroblotted to polyvinylidene membranes for immunoblotting with an antibody specific for the γ chain of fibrin and an antibody specific for the carboxy-terminus of α2AP.

To inhibit the crosslinking of α2AP to fibrin, a polypeptide spanning the crosslinking site on the amino terminus of α2AP (SEQ ID NO:2) was synthesized. The purity of the polypeptide was analyzed by high performance liquid chromatography, and its composition was verified by amino acid analysis on a Waters Picotag system. The α2AP polypeptide was then solubilized in 20 mM Tris-HCl and the pH was adjusted to 7.0. Various concentrations of polypeptide (7.5 μl, 0–5 mM final) were mixed with 20 μl of plasma, 1.25 μl of calcium chloride (0.4 mM), and 1.25 μl of thrombin (10.0 units/ml) and clotted for 90 minutes at 37° C. as described above. The clots were solubilized and analyzed by immunoblotting as described above.

Evaluation of Fibrinolytic Resistance of Pulmonary Embolisms in vivo

Pulmonary embolisms were induced in ferrets using standard methods, e.g., that described in Butte et al., 1997, Circulation. 95:1886–1891). Male ferrets (weighing approximately 1 kg) were anesthetized with ketamine and acepromazine. After full anesthesia had been obtained, the jugular vein and carotid artery were exposed by an anterior midline incision and cannulated with 20G catheters. Pooled, citrated human plasma was mixed with $^{125}$I-fibrinogen to achieve a specific activity of approximately 1,000,000 cpm/ml. Individual clots were formed by mixing $^{125}$I-fibrinogen-labeled plasma (45 μl) with 2.5 μl of bovine thrombin (100 units/ml) and 2.5 μl of calcium chloride (0.4 M). In some experiments, antibody 9C11 (3.1 μl; 10 μg) was added to each mixture to inhibit factor XIII activity, or α2AP polypeptide (3 μl, 1.5 mM final concentration) was added to attenuate α2AP crosslinking. After incubation at 37° C. for 90 minutes, the clots were compressed and washed three times with saline to remove unbound protein. The radioactive content of the clots was measured in a gamma counter immediately before injection. Blood samples were drawn at base line and at the end of the experiment. Sodium iodide (10 mg) was injected to block thyroid uptake. Three clots were embolized into the lungs by injection through the internal jugular vein. Successful embolization was evinced by the accumulation of radioactivity in the thorax.

All animals received weight-adjusted heparin at 100 units/kg (bolus), a dose sufficient to keep the activated partial thromboplastin time (aPTT) above 150 seconds throughout the procedure. TPA was given as a continuous infusion over 2 hours (1 mg/kg in 5 ml of normal saline). Animals were observed for a total of 4 hours after pulmonary embolization and then killed by lethal injection of anesthesia or $CO_2$ inhalation. The thorax was dissected and all intrathoracic structures were removed for gamma counting to detect residual thrombi. The percentage of clot lysis was determined for each ferret by dividing the total residual radioactivity in the thorax by that in the initial thrombi. A total of 28 animals was studied; three were excluded because of anesthetic-related death, improper TPA infusion, and failed embolism.

Fibrinogen Assays

Blood samples were collected on $K_3$EDTA (0.15% solution, final concentration) with aprotinin (50 kallikrein units/ml). Platelet-poor plasma was obtained by centrifugation of whole blood and assayed for fibrinogen by a standard sodium sulfite method such as that described by Rampling et al. 1976, Clin Chim Acta. 67:43–52.

Statistical Tests

The data were analyzed by a one way analysis of variance followed by the Bonferroni-Dunn procedure for testing multiple comparisons.

Inhibition of Factor XIII Activity During Clotting

The factor XIIIa-mediated crosslinking of the γ chains of fibrin is a rapid process, and, in the presence of fibrin, the activation of factor XIII by thrombin is accelerated. Monoclonal antibody 9C11 fully inhibits all factor XIIIa-mediated crosslinking in primate plasmas. To determine the amount of 9C11 required for inhibiting factor XIII activity in the present studies, dose-related effects of 9C11 on fibrin-fibrin γ chain and α2-antiplasmin-fibrin crosslinking during clotting were examined. In comparison with clots formed in the absence of inhibitor or in the presence of the nonspecific alkylating agent, iodoacetamide, clots formed with 9C11 at doses of 5 and 10 μg/clot showed no significant fibrin-fibrin γ chain or α2AP-fibrin crosslinking. A 9C11 dose of 10 μg was used for the experiments described below.

Selective Inhibition of α2AP Crosslinking to Fibrin

α2AP polypeptides, e.g., a polypeptide with the amino acid sequence of SEQ ID NO:2, were found to selectively inhibit factor XIIIa-mediated crosslinking of α2AP to fibrin. In comparison with clots formed in the absence of the α2AP peptide, clots formed in the presence of the polypeptide at concentrations of 0.38 mM and higher showed progressively less α2AP-fibrin crosslinking. At peptide concentrations of 1.5 mM and 3.0 mM, little α2AP crosslinking was visible.

In contrast, the α2AP polypeptide had no apparent effect on the formation of fibrin γ—γ crosslinks. Because the 1.5 mM concentration of the polypeptide strongly inhibited α2AP-fibrin crosslinking without preventing formation of the γ dimer, it was used in studies of the fibrinolytic effects of α2AP crosslinked to fibrin.

Role of Factor XIII Activity in Endogenous Lysis

To determine the importance of factor XIII in endogenous fibrinolysis (i.e., lysis caused by the ferret's own fibrinolytic system), the rates of dissolution of pulmonary emboli in animals treated with and without factor XIII inhibitor was measured. All animals received heparin at a weight-adjusted bolus of 100 units/kg; this dose was sufficient to keep the aPTT above 150 seconds throughout the experiment. Lysis of pulmonary emboli in the control group was 14.1±4.8% (mean±SD). Lysis of pulmonary emboli in the group treated with factor XIII inhibitor was three times as much (42.7±7.4%; p<0.0001). These data indicate that inhibition of factor XIII activity markedly increased endogenous lysis in these pulmonary emboli.

Role of Factor XIII Activity in Pharmacologic Lysis

The effect of factor XIII activity on the fibrinolytic resistance of pulmonary emboli in ferrets treated with TPA (1 mg/kg) was determined. TPA was administered over a time period of 2 hours, a regimen similar to that used to treat pulmonary embolism in humans. As above, all animals were treated with heparin, the standard therapy for human pulmonary embolism. One experimental group received pulmonary emboli with normal factor XIII levels, another pulmonary emboli in which both factor XIIIa-mediated fibrin-fibrin and α2AP crosslinking had been quenched by 9C11, and a third pulmonary emboli in which the crosslinking of α2AP to fibrin had been selectively inhibited by α2AP polypeptide.

Figure 1B:
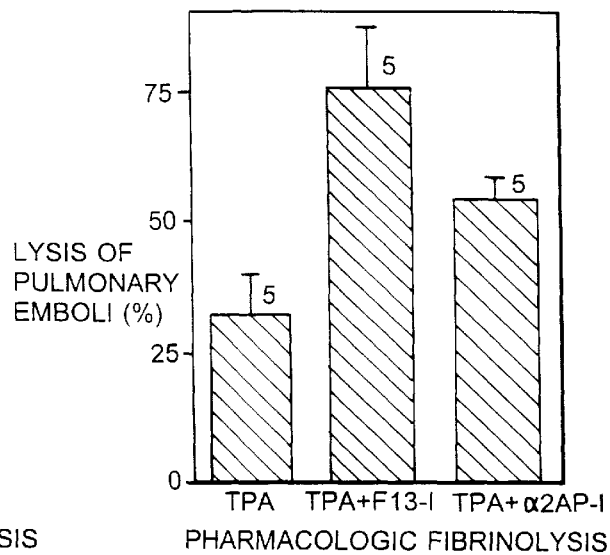

In the group with normal factor XIII activity, TPA caused more lysis (TPA, 32.3±7.7%) than was seen in the group that received no plasminogen activator (control, 14.1±4.8%; p<0.005) (FIGS. 1A–1B). Also, there was a nonsignificant trend (evaluated by the Dunn-Bonferroni correction) to more fibrinolysis in the group that received the factor XIII inhibitor but no TPA (FIGS. 1A–1B, F13-I) in comparison with the group with normal factor XIII activity that received TPA (42.7±7.4% vs 32.3±7.7%; p<0.05). Overall, factor XIII activity was an important determinant of fibrinolysis in animals treated with TPA because the factor XIII inhibitor group (FIG. 1B, TPA+F13I) showed significantly more lysis than the group with normal factor XIII activity (76.0±11.9% vs 32.3±7.7%; p<0.0001). In particular, factor XIIIa-mediated crosslinking of α2AP to fibrin made a specific contribution to fibrinolytic resistance because selective inhibition of this crosslinking also significantly accelerated lysis by TPA (FIG. 1B, TPA+α2AP-I) in comparison with lysis in animals with normal factor XIII activity (54.7±3.9% vs 32.3±7.7%; p<0.0005). Still, selective inhibition of α2AP-fibrin crosslinking was less effective at amplifying lysis than was inhibition of all factor XIIIa-mediated crosslinking (54.7±3.9% vs 76.0±11.9%; p<0.0005), suggesting that fibrin-fibrin crosslinking also contributed to fibrinolytic resistance.

Effects on Fibrinogen Levels

Figure 2:
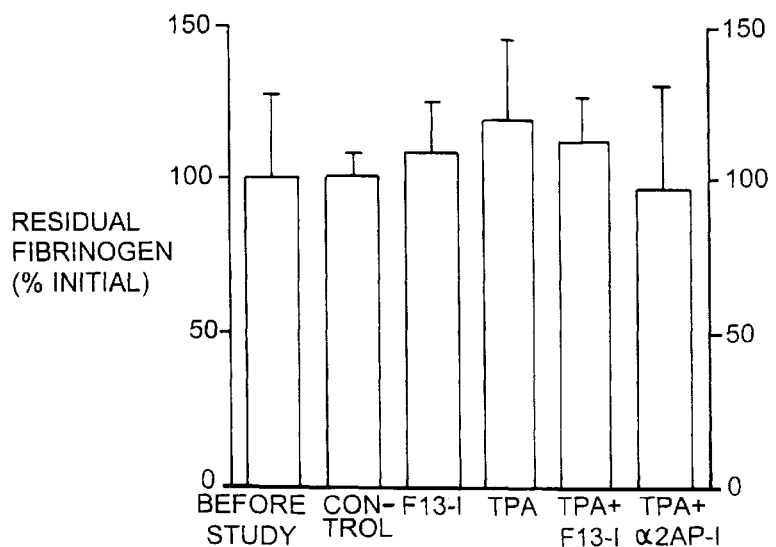
FIG. 2 is a bar graph showing the effects of factor XIIIa activity and TPA on residual fibrinogen levels. Fibrinogen levels were measured in 25 ferrets by sodium sulfite precipitation and expressed as a percentage of the fibrinogen level prior to the experiments ("before study" level was defined as 100%). The percent residual fibrinogen level (mean±SD) is shown for each group of 5 ferrets at the end of the experiment. The following conditions were evaluated: Control, normal factor XIIIa activity, no TPA; F13-I, factor XIIIa inhibited, no TPA; TPA, TPA with normal factor XIIIa activity; TPA+F13-I, TPA with inhibited factor XIIIa activity; TPA+α2AP-I, TPA with inhibited α2 antiplasmin-fibrin crosslinking.

To determine whether the inhibition of total factor XIII activity or the selective inhibition of α2AP-fibrin crosslinking enhanced the systemic degradation of the clotting factor fibrinogen during fibrinolysis, fibrinogen levels were measured for all animals before and after treatment. FIG. 2 shows a comparison of the residual fibrinogen levels at the end of the study for each group, expressed as a percentage of the initial fibrinogen value. There was no significant decrease in fibrinogen levels (below 100%) for any of the experimental groups. These data indicate that nonspecific degradation of fibrinogen did not occur when TPA was administered alone, in combination with inhibition of factor XIII, or in combination with inhibition of α2AP crosslinking.

These data indicate the α2AP polypeptides selectively inhibit endogenous α2AP-fibrin crosslinking (and therefore, enhance endogenous and therapeutic fibrinolysis of pulmonary emboli) in an established art-recognized model of pulmonary embolism in ferrets. To simulate the standard therapy for humans with pulmonary embolism, and to inhibit the accretion of new thrombus on these emboli, all animals were given doses of heparin sufficient to significantly prolong the aPTT (>150 seconds) throughout the experiment. Inhibition of factor XIIIa activity tripled the rate of endogenous fibrinolysis (42.7±7.4 vs 14.1±9.8%). This was a profound effect because the amount of endogenous lysis in clots with inhibited factor XIIIa activity was as much as, or perhaps slightly more than, the amount induced by TPA in clots with normal factor XIIIa activity (32.2±7.7%). A parallel enhancement was seen in the lysis of pulmonary emboli by TPA (1 mg/kg): inhibition of both factor XIIIa fibrin-fibrin and α2-antiplasmin-fibrin crosslinking substantially increased lysis (76.0±11.9%) over that seen with the same dose of TPA alone (32.3±7.7%). In addition, selective inhibition of α2AP-fibrin crosslinking amplified TPA-induced lysis (54.7±3.9%) in comparison with that induced by TPA alone (32.3±7.7%). This effect underscores the inhibitory role played by the crosslinking of α2AP to fibrin during initiation of fibrinolysis. That even higher fibrinolysis was achieved with TPA when factor XIIIa-mediated fibrin-fibrin crosslinking and α2AP-fibrin crosslinking were both inhibited fully (76.0±11.9%) indicates that both crosslinking processes contribute to inhibition of fibrinolysis induced by TPA.

If full heparinization did not completely prevent the absorption and activation of ferret factor XIII onto these clots after embolization, some degree of crosslinking may have occurred in the thrombi of all experimental groups. The effect of this crosslinking would be to blunt the increased fibrinolysis attributed to the factor XIII inhibitors. This would not change the conclusion that factor XIIIa crosslinking is a major cause of fibrinolytic resistance, but would imply that its role is even larger than was observed in these experiments.

In vitro studies suggested that fibrin-crosslinked α2AP plays a role in the susceptibility of plasma clots to fibrinolysis. An N-terminal peptide of α2AP was reported to inhibit α2AP-fibrin crosslinking, but the peptide used did not compete efficiently with α2AP for specific crosslinking to fibrin. The α2AP polypeptides described herein specifically and efficiently inhibit α2AP-fibrin crosslinking. The level of inhibition achieved with the polypeptide described herein is at least 50% greater than that observed with previously-described peptides, e.g., as measured by the method of Ichinose et al., 1983, FEBS Letters 153:369–371.

The Catalytic Half-life of Activated Factor XIII in Thrombi

To examine whether unremitting crosslinking by activated factor XIII (FXIIIa) contributes to the increased fibrinolytic resistance of older thrombi, the persistence of FXIIIa activity in human clots of various ages was examined.

FXIIIa activity was measured with 1) full-length α2AP, a physiologic glutamine substrate; 2) α2AP$_{13-24}$ (SEQ ID NO:2); and 3) pentylamine, a nonspecific lysine substrate.

The crosslinking of α2AP and α2AP$_{13-24}$ (SEQ ID NO:2) into fibrin by clot-bound FXIIIa declined with half-lives of approximately 62 and 72 minutes, respectively. Mutational studies showed that glutamine 14 (but not glutamine 7 or 16) and valine 17 of α2AP were required for fibrin crosslinking. FXIIIa crosslinking of pentylamine into fibrin also declined with a half-life of 173 minutes. The loss of activity was not due to FXIIIa proteolysis and was partially restored by reducing agents, indicating that oxidation inhibits the enzyme over time. The physiologic persistence of FXIIIa activity in thrombi was confirmed by the crosslinking of an infused α2AP$_{13-24}$ peptide into existing pulmonary emboli in vivo. This crosslinking was significantly attenuated when thrombus-associated FXIIIa was inhibited.

FXIIIa crosslinks α2AP and an α2AP peptide, in a sequence-specific manner, into formed clots with a catalytic half life of approximately 1 hour. These findings indicate a preferred therapeutic window for administration of FXIIIa inhibitors. The data also indicate that the catalytic activity of FXIIIa can be exploited to specifically target newly formed thrombi.

Assays of FXIIIa Catalytic Half-life and Substrate Specificity

Experiments were performed to determine how long FXIIIa in clots could crosslink various substrates such as human $^{125}$I -α2AP, α2AP$_{13-24}$ (SEQ ID NO:2), and 5-(biotinamido)pentylamine, into fibrin. In a typical experiment, clots were prepared (50 μl final volume) in duplicate by combining fibrinogen (2 mg/ml final), CaCl$_2$ (2 mM final), buffer (Tris-buffered saline pH 7.4) and thrombin (1 U/ml) and incubating at 37° C. Synchronous with the addition of thrombin, or up to 240 minutes afterwards, the FXIIIa substrates 5-(biotinamido)pentylamine (0.5 mM final), $^{125}$I -α2AP (70 μg/ml final), and α2AP$_{13-24}$ (0 to 1 mM final) were mixed and added to the clot. In one set of control samples, FXIIIa was inhibited with iodoacetamide (10 mg/ml) prior to the addition of substrate; to another set, no substrate was added. After 2 hours of incubation at 37° C., iodoacetamide (10 mg/ml) was added to stop the reaction. The tubes were then centrifuged at 14,000 rpm for 2 minutes, washed and compressed in 1 ml saline to remove unbound proteins, and centrifuged again at 14,000 rpm for 2 minutes. After removal of the supernatant, the clots were solubilized in 100 μL of 9M urea, pH 9.0 at 37° C. for 60 minutes. Then 100 μl of SDS reducing sample buffer was added and the clots were placed at 85° C. for 30 minutes until fully solubilized. The samples were examined by SDS-PAGE. Crosslinked $^{125}$I-α2AP was detected and quantitated by phosphorimaging. Samples containing crosslinked α2AP$_{13-24}$ and pentylamine substrates were electroblotted to PVDF membranes and detected by $^{125}$I-streptavidin followed by phosphorimaging or by streptavidin-peroxidase followed by the developing agents 5-bromo-4-chloro-3-indolyl phosphate-nitro blue tetrazolium using methods known in the art. In experiments examining the effect of specific amino acid residues on the crosslinking of the α2AP$_{13-24}$ peptide (SEQ ID NO:2) to fibrin, crosslinking was detected by immunoblotting with an anti-peptide antibody directed against this epitope followed by $^{125}$I-protein A and phosphorimaging. In some experiments, clots were formed by mixing 25 μl pooled human fresh frozen plasma with 25 μl 30 mM CaCl$_2$ instead of using human fibrinogen.

To examine the potential degradation of FXIIIa in clots, samples from these experiments were immunoblotted with a monoclonal antibody directed against the alpha subunit of FXIII.

Crosslinking of α2AP$_{13-24}$ into Fibrin by FXIIIa and Tissue Transglutaminase Fibrin clots (50 μl) were prepared in duplicate by mixing FXIII-free fibrinogen (2 mg/ml final), α2AP$_{13-24}$ (SEQ ID NO:2; 0.5 mM final), CaCl$_2$ (2 mM final), human plasma FXIII (100 nM/L final) and guinea pig tissue transglutaminase (100 nM/L final) and thrombin (1 U/ml final) and incubating at 37° C. for 2 hours. The crosslinking of α2AP$_{13-24}$ was detected as described above.

Crosslinking of α2AP$_{13-24}$ into Pulmonary Emboli in vivo

To examine whether FXIIIa which formed thrombi in vivo retained the ability to crosslink substrates, the ferret pulmonary embolism model was used. Clots were formed by combining 45 μl of pooled human fresh frozen plasma with $^{125}$I-labeled fibrinogen (~100,000 cpm/clot), 2.5 μl of 0.4 M CaCl$_2$, and 2.5 μl thrombin (1000 U/ml). The clots were incubated at 37° C. for 20 minutes, washed three times in saline, and 6 were embolized into the lungs of each animal. Three experimental groups were examined with 2 animals in each group. One group received normal clots and a solution of α2AP$_{13-24}$ (SEQ ID NO:2) calculated to produce a final peptide concentration of 0.5 mM. Another group also received the same peptide concentration; prior to embolization, the clots in this group were washed in iodoacetamide (10 mg/ml) and EDTA (10 mM final) to inhibit clot associated FXIIIa. The third group received the blood clots but no peptide infusion afterward. Four hours after embolization, the ferrets were sacrificed by CO$_2$ inhalation. The heart, lungs, and great vessels were removed and gamma-counted to locate the pulmonary emboli.

Lung tissue containing pulmonary emboli was localized with a Geiger counter, excised and weighed. Samples were homogenized in 200 μl of a buffer containing 24 mM Tris Base, 476 mM Tris HCl, 50 mM MgCl$_2$, 1 mg/ml DNase I, and 0.25 mg/ml RNAase A, allowed to sit on ice for 10 minutes, centrifuged at 12,000 rpm at 4° C. for 20 minutes, the supernatant was removed and the pellet was dissolved in 200 μl of sample buffer, mercaptoethanol, and bromophenol blue, and, finally boiled for 20–30 minutes until dissolved. The samples (100 μg/lane) were then subjected to 7.5% SDS-PAGE, transferred to PVDF membranes, blocked with milk, washed, and incubated with streptavidin horseradish peroxidase (1:1000) for 1 hour, washed, incubated with a chemiluminescent substrate and exposed to film.

Histology

Lung tissue was immersed in 30% sucrose overnight, embedded in OCT and cut into 10 micron sections. The sections were fixed in 100% methanol for 5 minutes at room temperature. For the detection of fibrin, the samples were treated with 3% H$_2$O$_2$ for 20 minutes at room temperature, washed in PBS 3 times, treated with 10% goat normal serum for 20 minutes at room temperature. The samples were then treated with a primary polyclonal goat anti-human fibrin antibody (1:400 dilution, 2.5 μg/ml) at 4° C. overnight, washed 2 times in high salt PBS and once in regular PBS. The sections were then incubated in a secondary goat anti-rabbit peroxidase-labeled antibody (1:100) for one hour at room temperature, washed in PBS 3 times, developed in DAB (3,3'-diaminobenzidine), counterstained in 0.1% methyl green, and mounted.

For the detection of α2AP$_{13-24}$ (SEQ ID NO:2), endogenous peroxidase was quenched with 3% H$_2$O$_2$ in 100% methanol for 20 minutes at room temperature, washed in PBS 3 times. The ABC (avidin-biotin complex) reagent was applied to the section for one hour at room temperature, washed in PBS 3 times, developed in DAB substrate, counterstained in 0.1% methyl green, and mounted.

FXIIIa Half-life Determination

To examine the catalytic half-life of FXIIIa in thrombi, the crosslinking of α2AP (FXIIIa's physiologic macromolecular substrate) was measured. The greatest amount of crosslinking of $^{125}$I-α2AP occurred when it was added synchronously with thrombin to fibrinogen to initiate clotting. Thereafter, the amount of α2AP crosslinking dropped off rapidly until almost no crosslinking was detected at 80 minutes, particularly when compared to controls in which FXIIIa has been inhibited with iodoacetamide, or in experiments containing no $^{125}$I-α2AP. Semilog plots of the decay of crosslinking of $^{125}$I-α2AP to fibrin by FXIIIa indicated a half-life of 62 minutes ($r^2$=0.92), consistent with an exponential decline in catalytic activity.

One potential explanation for the marked decline in the crosslinking of α2AP to fibrin was that the size of α2AP (70,000 Da) inhibited its diffusion into the assembling fibrin meshwork. To examine this possibility, a peptide that mimicked the region of α2AP (α2AP$_{13-24}$ (SEQ ID NO:2)) that contains the glutamine residue which is crosslinked to fibrin was used. To permit detection, the peptide was biotinylated at lysine 24. The small size of this peptide (1600 Da) readily permits diffusion into a developing thrombus. This peptide and the variant peptides described herein inhibit the crosslinking of α2AP to fibrin when added during clotting. The inhibitory peptides crosslinked into fibrin clots in a dose-dependent manner. The most exuberant crosslinking of the peptide occurred to proteins with the apparent molecular sizes of 60–70 kDa, though crosslinking into proteins of 50 kDa, 90 kDa, and 120 kDa and above was also seen at high concentrations. When compared to control clots, crosslinking of the α2AP$_{13-24}$ (SEQ ID NO:2) peptide is seen at concentrations as low as 1.3 µM, reaches half of maximum crosslinking at 110 µM and appears to saturate at concentrations of 0.33 to 1 mM. A similar dose response curve was found for the crosslinking of the α2AP$_{13-24}$ (SEQ ID NO:2) peptide to fibrin in plasma.

Figure 3A:
FIG. 3A is a diagram showing the amino acid sequences of the native α2AP$_{1-24}$ amino-terminal peptide and related peptides containing specific amino acid substitutions. The top line shows the sequence of the native α2AP$_{13-24}$ amino-terminal peptide (SEQ ID NO:2) used for FXIIIa crosslinking studies. The arrow indicates the glutamine residue in SEQ ID NO:2 which is crosslinked by FXIIIa to fibrin. α2AP$_{1-24}$ (SEQ ID NO:16) and α2AP variants (SEQ ID NO:11, 12, 13, 14, and 15) are also shown.
Figure 3B:
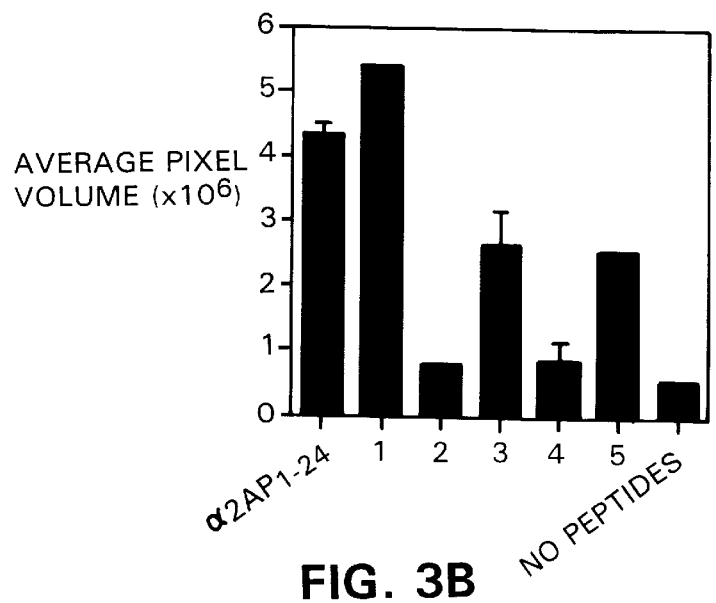
FIG. 3B is a bar graph showing crosslinking of α2AP$_{1-24}$ and the variant α2AP peptides from shown in FIG. 3A to fibrin clots. A 0.5 mM concentration of each peptide was clotted with human fibrinogen. After electrophoresis of the solubilized, reduced clots on 7.5% SDS-PAGE gels and transfer to PVDF membranes, the extent of crosslinking of each peptide was determined by incubating the membranes with a polyclonal antibody directed against the amino-terminus of α2AP, followed by incubation in $^{125}$I-protein A, and exposure in a phosphorimager. Each bar reflects phosphorimage quantification of the fibrin crosslinking α2AP$_{1-24}$ and the variant peptides. The mean±SD pixel volume of the quantified blots are shown.

Although FXIIIa can crosslink a number of lysine analogs to glutamine sites in macromolecules such as fibrin, its specificity for crosslinking glutamine-containing substrates (acyl donors) such as α2AP to fibrin has not been defined. To examine specificity, a wild-type α2AP fragment spanning residues 1–24 (MEPLGWQLTS GPNQEQVSPL TLLK; SEQ ID NO:16) and a panel of α2AP variant peptides (corresponding to residues 1–24 with the exception that one residue is altered from the wild type sequence; SEQ ID NO:11, 12, 13, 14, 15) was created with mutations of residues that represented other potential crosslinking sites or residues that are conserved among different α2APS from different species. FIG. 3A shows the sequences of the wild-type and variant peptides. By comparison to clots containing no peptide or the wild type peptide α2AP$_{1-24}$, peptides containing mutations Q14A (SEQ ID NO:12) and V17N (SEQ ID NO:14) were not efficiently crosslinked to fibrin (FIG. 3B). In contrast, α2AP peptides with mutations at E15A (MEPLGWQLTS GPNQAQVSPL TLLK; SEQ ID NO:17), Q16A (MEPLGWQLTSGPNQEAVSPLTLLK; SEQ ID NO:13) and L22N (MEPLGWQLTSGPNQEQVSPLTNLK; SEQ ID NO:15) were crosslinked into fibrin at rates comparable to that of the wild type α2AP1-24 peptide (SEQ ID NO:16). These variant peptides (as well as Q7A (MEPLGWALTSGPNQEQVSPLTLLK; SEQ ID NO:11) and peptide mimetics thereof are suitable for use in the diagnostic and therapeutic applications described herein.

Similar results were seen when these peptides were used as inhibitors of the crosslinking of α2AP$_{13-24}$ (SEQ ID NO:2) into fibrin: all peptides but Q14A and V17N competed for crosslinking. Taken together, these results indicate that α2AP$_{1-24}$ (SEQ ID NO:16) and α2AP$_{13-24}$ (SEQ ID NO:2) are specific glutamine substrates for FXIIIa and indicate that Q14 and V17 are necessary for efficient fibrin crosslinking. While FXIIIa is the primary transglutaminase found in plasma, other transglutaminases are found in cells that do not require thrombin for activation. Additional experiments were carried out to determine whether the α2AP$_{13-24}$ (SEQ ID NO:2) peptide is efficiently crosslinked by tissue transglutaminase. In studies with purified, FXIIIa-deficient fibrinogen, there was little, if any, significant crosslinking of the α2AP$_{13-24}$ (SEQ ID NO:2) peptide to fibrin with clotting. Addition of purified tissue transglutaminase (100 nM) caused a slight increase in crosslinking, whereas addition of equivalent amounts of purified exogenous FXIIIa caused significantly more crosslinking of the α2AP$_{13-24}$ peptide to fibrin. Moreover, in experiments with purified human fibrinogen, the potent thrombin inhibitor hirudin blocked α2AP$_{13-24}$ peptide-fibrin crosslinking. These data indicate that FXIIIa is responsible for the crosslinking of the α2AP$_{13-24}$ peptide in these fibrinogen preparations because it is the only thrombin-dependent transglutaminase.

Because the α2AP$_{13-24}$ peptide was a selective FXIIIa substrate that should be readily permeable to the fibrin clot because of its small size, it was used to measure the catalytic life of FXIIIa in formed or forming clots. Consistent with experiments performed with $^{125}$I-α2AP, the crosslinking of α2AP$_{13-24}$ (SEQ ID NO:2) to fibrin was greatest when it was present at the initiation of clotting (t=0). The relative amount of crosslinking fell rapidly over the course of an hour to nearly undetectable levels. The half-life calculated for α2AP$_{13-24}$ crosslinking from these studies was 72 minutes ($r^2$=0.998) which was comparable to that found for the $^{125}$I-α2AP.

To determine whether FXIIIa showed a similar catalytic half-life for a lysine (acyl acceptor) mimic (pentylamine-biotin, an even smaller substrate than α2AP$_{13-24}$ (SEQ ID NO:2)), pentylamine-biotin was crosslinked into fibrin clots. The half-life was 173 minutes ($r^2$=0.774), which is nearly 2.3–2.8 times longer than was seen with α2AP or α2AP$_{13-24}$ (SEQ ID NO:2). Since proteolysis of FXIIIa at a second thrombin site has been described to inactivate the enzyme, studies were carried out to determine whether the proteolytic fragmentation accounts for the loss of FXIIIa activity in these clots. There was no significant increase in the relative amounts of the smaller FXIIIa fragment (56 kDa) versus FXIIIa (80 kDa). These data indicate that proteolysis alone does not explain the marked decline in FXIIIa activity. Since the FXIIIa contains multiple reduced cysteines, including the active site residue, dithiothreitol (DTT) was added to the reaction mixtures to determine whether the loss in catalytic activity of the molecule could be restored by the addition a reducing agent. Under normal circumstances, when pentylamine or α2AP$_{13-24}$ (SEQ ID NO:2) was added to 2 or 4 hour old clots, there was little residual FXIIIa crosslinking. However, by comparison DTT, restored the crosslinking of pentylamine or α2AP$_{13-24}$ to fibrin clots. These data indicate that reversible oxidation of FXIIIa rather than proteolysis is responsible for the precipitous loss of enzymatic function.

To confirm the physiologic significance of these findings, the ability of FXIIIa to crosslink α2AP$_{13-24}$ (SEQ ID NO:2) in vivo to existing pulmonary emboli was examined. Three experimental groups were studied: a control group that received no peptide after embolism of preformed clots and two experimental that groups received a 0.5 mM dose of α2AP$_{13-24}$ (SEQ ID NO:2) peptide after embolization of normal clots or clots that were pretreated with iodoacetamide and EDTA to inhibit residual clot-associated FXIIIa.

After 4 hours, the animals were sacrificed and portions of the lung containing the $^{125}$I-fibrin-labeled thrombi or no thrombi were isolated, weighed and analyzed. Pulmonary emboli occluded pulmonary arterioles Immunostaining with a polyclonal anti-fibrin antibody confirmed that the pulmonary arteriole occlusion was a thrombus. Histologic sections from animals that received emboli with normal FXIIIa activity with or without the $\alpha 2AP_{13-24}$ (SEQ ID NO:2) peptide after embolization were also examined. These histologic sections were probed with avidin-peroxidase to detect the thrombus associated $\alpha 2AP_{13-24}$ (SEQ ID NO:2) biotinylated peptide. When compared to a control thrombus (middle panel) from an animal not receiving $\alpha 2AP_{13-24}$ (SEQ ID NO:2), specific staining was detected in the thrombus from an animal receiving the peptide infusion, indicating incorporation of the $\alpha 2AP_{13-24}$ (SEQ ID NO:2) into the thrombus.

Lung tissue samples were subjected to SDS-PAGE and blotted with $^{125}$I-streptavidin to detect biotinylated $\alpha 2AP_{13-24}$ (SEQ ID NO:2) and stained by Coomassie blue to confirm that the peptide was covalently incorporated into fibrin in the thrombus. Lung tissue from control animals (normal emboli and no $\alpha 2AP_{13-24}$ (SEQ ID NO:2)) showed two nonspecific avidin binding bands at ~70 kDa and ~120 kDa in both the embolus-containing and non-embolus containing tissues. In animals receiving the $\alpha 2AP_{13-24}$ (SEQ ID NO:2) peptide, there were similar non-specific staining bands at 70 kDa and 120 kDa in the lung tissue without emboli. However, the lung tissue containing pulmonary emboli showed a new broad band at ~65–70 kDa, and additional bands at 60 kDa, ~100 kDa and ~140 kDa. The intensity of the bands was diminished in the lung tissue from an animal with a pulmonary embolus in which the thrombus associated FXIIIa had been inhibited by iodoacetamide and EDTA (lane 3). Taken together, these data indicate that $\alpha 2AP$ fragments (e.g., amino-terminal $\alpha 2AP$ fragments and variants thereof) are crosslinked into preexisting pulmonary embolus in vivo and that crosslinking is attenuated by inhibition of the FXIIIa in the thrombus.

The finding that FXIIIa crosslinking causes fibrinolytic resistance in new pulmonary emboli underscores the importance of FXIIIa regulation, and indicates that continued FXIIIa crosslinking contributes to the time-related increase in fibrinolytic resistance of thrombi with age. In clots, the catalytic ability of FXIIIa to crosslink a physiologic glutamine substrate ($\alpha 2AP$, 70 kDa), or a small peptide fragment of that substrate ($\alpha 2AP_{13-24}$ (SEQ ID NO:2), 1.6 kDa), declines in a negative exponential fashion with calculated half-lives of 62 and 72 minutes, respectively. The comparable half-lives of these two substrates, despite marked differences in size, indicates that crosslinking of $\alpha 2AP$ was not simply limited by its permeation into the fibrin clot. The ability of FXIIIa to crosslink a lysine substrate analog pentylamine-biotin also declined in a negative exponential fashion but with a longer half-life of 173 minutes. The decline in catalytic activity of FXIIIa could not be ascribed to proteolysis of the catalytic subunit FXIIIa, but was related to potential oxidation. FXIIIa contains an active site cysteine residue that is known to be vulnerable to inhibition by oxidation. The relative 'restoration' of FXIIIa crosslinking in older clots of the $\alpha 2AP_{13-24}$ (SEQ ID NO:2) peptide by reducing agents, was significantly less marked than was the restoration of crosslinking of the pentylamine-biotin substrate, suggesting that the number of sites available for crosslinking of the $\alpha 2AP_{13-24}$ substrate may actually be limiting in these older clots. In vivo studies confirmed in vitro findings by demonstrating that formed pulmonary emboli (30 minutes old) covalently incorporated $\alpha 2AP_{13-24}$ (SEQ ID NO:2) peptide. This incorporation was largely due to the enzymatic activity of the thrombus-bound FXIIIa as it was significantly attenuated in thrombi in which FXIIIa had been inhibited immediately prior to embolization. Although previous studies have examined the clearance of circulating FXIII zymogen in deficient patients, these data represent the first estimates of the catalytic life of FXIIIa in clots.

FXIIIa makes thrombi resistant to plasmin by modifying the fibrin matrix through intermolecular crosslinks. FXIIIa mediated fibrin $\alpha$-chain polymerization, and $\gamma$-chain multimerization contributes to this fibrinolytic resistance. In addition, the crosslinking of the potent plasmin inhibitor $\alpha 2AP$ to fibrin plays a clear role in neutralizing fibrinolysis. In vitro, the crosslinking of $\alpha 2AP$ to fibrin and the formation of $\gamma$-dimers occurs rapidly within 2–5 minutes. However, $\alpha$-chain polymerization occurs more slowly and fibrin $\gamma$-chain multimerization takes hours to days. Experimental studies of rabbit thrombi formed in vivo confirm that $\gamma$-chain dimerization and $\alpha$-chain polymerization is readily seen within 7 to 9 minutes of thrombus formation, though small increments in $\alpha$-chain polymerization can be detected after 90 to 320 minutes. There are limited studies of the fibrin structure of human thrombi, but when examined ex vivo, all showed evidence of complete $\alpha$-chain polymerization, though the ages of these thrombi were not well specified.

Crosslinking by FXIIIa is highly specific because only a minority of potential glutamines and lysines in proteins are actually substrates. The primary structure, charge, and conformation around the respective glutamine residues determine the suitability of a peptide-bound glutamine as a substrate for FXIIIa. Of the 3 potential glutamine sites in the amino-terminus of the $\alpha 2AP_{13-24}$ peptide, only glutamine 14 is required. In addition, Val17, which is highly conserved in other species $\alpha 2AP$ also appears to be required. Further, although purified tissue transglutaminase can crosslink the $\alpha 2AP_{13-24}$ peptide into fibrin, much as it can crosslink fibrin chains together it does so at a lower rate than equivalent amounts of FXIIIa. Moreover, the crosslinking of the $\alpha 2AP_{13-24}$ (SEQ ID NO:2) peptide into fibrin and plasma clots requires thrombin activity, a property that signifies the involvement of FXIIIa.

These data indicate that FXIIIa, in 30 minute-old emboli, retains the catalytic ability to incorporate a specific substrate into fibrin. The observation that FXIIIa remains catalytically active only in recent thrombi is useful to detect or target therapies to 'new' thrombi. An advantage of the diagnostic and therapeutic approaches described herein is that they are not affected by treatment with conventional anticoagulants such as heparin or warfarin because they do not affect FXIIIa activity. The ability to distinguish new from old thrombi could significantly improves the specificity of fibrinolytic therapy and permits targeting therapeutic compositions to recently formed clots. The compositions are also useful to prevent future thrombotic events.

Therapeutic Applications $\alpha$2-antiplasmin causes resistance to endogenous as well as pharmacologic fibrinolysis in venous thromboemboli in vivo. It is likely that other molecular factors in the thrombus (e.g., PAI-1 and $\alpha$2-antiplasmin) cause the fibrinolytic resistance seen in thrombotic diseases such as pulmonary embolism.

In humans, pulmonary emboli appear to develop from the fragmentation of propagating thrombi in the deep venous system. Anticoagulants that interfere with the activity of thrombin, prevent thrombus propagation by inhibiting the new deposition of fibrin. Still, despite effective anticoagulation, the inherent fibrinolytic resistance of formed thrombi prevents optimal treatment of patients with thrombotic disease. In studies of heparinized animals described above, factor XIIIa-mediated crosslinking was found to play a critical role in limiting the endogenous and pharmacologic fibrinolysis of formed experimental pulmonary emboli. These data indicate that factor XIII inhibitors such as the α2AP polypeptides described herein are useful for the treatment of thrombotic disease.

α2AP polypeptides will ordinarily be at least about 12 amino acids, usually about 20 contiguous amino acids, preferably at least 40 contiguous amino acids, more preferably at least 50 contiguous amino acids, and most preferably at least about 60 to 80 contiguous amino acids in length. Such peptides can be generated by methods known to those skilled in the art, including proteolytic cleavage of the protein, de novo synthesis of the fragment, or genetic engineering, e.g., cloning and expression of a fragment of α2AP-encoding cDNA. For example, chimeric therapeutic agents in which an N-terminal α2AP polypeptide is linked to a thrombolytic agent such as TPA can be recombinantly produced by cloning DNA encoding the α2AP portion of the chimera in frame to DNA encoding TPA (or another therapeutic agent) into a suitable expression vector and expressing the recombinant chimeric protein in eucaryotic or procaryotic cells using standard expression technology. DNA sequences encoding mammalian α2AP (such as human, bovine, and mouse α2AP) and encoding such thrombolytic agents as TPA are publicly available from databases such as GENBANK™.

Variants of α2AP polypeptides described above (e.g., those containing the amino acid sequences of SEQ ID NO:1–7) may also be used provided that they have the activity of inhibiting α2AP-fibrin crosslinking. Variants can differ by amino acid sequence (e.g, conservative amino acid substitutions, e.g., those shown in Table 4), or by modifications which do not affect the sequence, or both.

TABLE 4

CONSERVATIVE AMINO ACID SUBSTITUTIONS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans- |

TABLE 4-continued

CONSERVATIVE AMINO ACID SUBSTITUTIONS

| For Amino Acid | Code | Replace With |
|---|---|---|
| Proline | P | 3,4, or 5-phenylproline, AdaA, AdaG, cis-3,4, or 5-phenylproline, Bpa, D-Bpa D-Pro, L-I-thioazolidine-4-carboxylic acid, D-or L-1-oxazolidine-4-carboxylic acid (Kauer, U.S. Pat. No. (4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

To render the therapeutic peptides less susceptible to cleavage by peptidases, the peptide bonds of a peptide may be replaced with an alternative type of covalent bond (a "peptide mimetic"). Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptide mimetics. Where proteolytic degradation of the peptides following injection into a mammalian subject, e.g., a human patient, is a problem, replacement of a particularly sensitive peptide bond with a noncleavable peptide mimetic bond will make the resulting peptide more stable, and thus more useful as a therapeutic agent. Such mimetics, and methods of incorporating them into polypeptides, are well known in the art. Similarly, the replacement of an L-amino acid residue with a D-amino acid is a standard way of rendering the polypeptide less sensitive to proteolysis. Also useful are aminoterminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Peptides may be administered to the patient intravenously in a pharmaceutically acceptable carrier such as physiological saline. Such methods are well known to those of ordinary skill in the art. It is expected that an intravenous dosage of approximately 1 to 100 μmoles of the peptide of the invention would be administered per kg of body weight per day. For diagnostic procedures, smaller peptides (e.g., 75 amino acids or less, preferably 50 amino acids or less, more preferably 25 amino acids or less, and most preferably 15 amino acids or less, in length) can be administered at mM concentrations because these shorter polypeptides are crosslinked at a faster rate than larger polypeptides and are cleared rapidly from the body.

The formulations of this invention are useful for parenteral administration, such as intravenous, subcutaneous, intramuscular, and intraperitoneal. Other methods of delivery, e.g., diffusion from a stent impregnated with therapeutic polypeptide or peptide mimetic, are known in the art.

Diagnostic Applications

Factor IIIa mediates α2AP-fibrin crosslinking in new or actively forming thrombi. As described above, the α2AP polypeptides described herein compete with endogenous α2AP, i.e., α2AP polypeptide also become incorporated into newly forming clots. Detectably-labelled α2AP polypeptides are therefore useful to non-invasively detect clot formation. The α2AP polypeptides are labeled with an imaging marker to permit detection. For in vivo imaging, the peptides are preferably labeled with a radioisotope such as a gamma-emitter, positron-emitter, or x-ray-emitter (including, e.g., indium-111, technetium-99m, iodine-125, gallium-67, and gallium-68). Alternatively, the polypeptide may be biotinylated (e.g., via a lysine residue of the polypeptide).

The labelled polypeptide is administered to a subject in a dose which is diagnostically effective. The term "diagnostically effective" means that the detectably labeled species is administered in sufficient quantity to enable detection of the blood clot. The concentration of detectably labeled species administered should be sufficient so the binding to thrombi is detectable compared to the background. For example, for diagnostic purposes, shorter polypeptides are preferable because the signal-to-noise ratio is better than that associated with longer peptides (e.g., over 75 amino acids in length). Further, it is desirable that the detectably labeled polypeptide be rapidly cleared from the circulatory system in order to give the best target-to-background signal ratio.

As a rule, the dosage of detectably labeled species for in vivo diagnosis will vary depending on such factors as age, sex, and extent of disease of the individual. For instance, the dosage of monoclonal antibody can vary from about 0.01 mg/M$^2$ to about 500 mg/M$^2$, preferably 0.05 mg/M$^2$ to about 200 mg/M$^2$, most preferably about 0.1 mg/M$^2$ to about 10 mg/m$^2$. Such dosages may vary, for example, depending on whether multiple injections are given, progression of the disease, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

The sites of localization may be determined by standard imaging techniques, preferably planar imaging or single photon emission computed tomography (SPECT), and by gamma camera imaging. In addition, the polypeptides can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, 52Cr, and $^{56}$Fe.

For in vivo diagnosis, radioisotopes may be bound to a polypeptide either directly or indirectly by using an intermediate functional group. Intermediate functional groups which often are used to bind radioisotopes which exist as metallic ions to immunoglobulins are the bi-functional chelating agents such as diethylenetriaminepentacetic acid (DTPA) and ethylenediaminetetraacetic acid (EDTA) and similar molecules. Typical examples of metallic ions which can be bound to polypeptides are $^{111}$In, $^{97}$Ru $^{67}$Ga $^{68}$Ga $^{72}$As, $^{89}$Zr, $^{90}$Y, and $^{201}$Tl.

The labelled α2AP polypeptide is administered to the patient in a pharmaceutically acceptable carrier and labeled with a marker to permit in vivo detection as described above. Pharmaceutically acceptable carriers useful for imaging and therapy are well-known in the art and include, for example, aqueous solutions such as bicarbonate buffers, phosphate buffers, Ringer's solution and physiological saline supplemented with 5% dextrose or human serum albumin, if desired.

Following administration of the labelled polypeptide (e.g., intravenously) to the subject, association of the polypeptide with a vascular obstruction is determined. Association, e.g., via crosslinking to fibrin, is an indication of the presence of blood clot formation at that site. Where the detecting step is quantitative, the amount of binding would correlate with and allow diagnosis of the severity of the disease. Furthermore, if the diagnostic method is carried out multiple times by repeatedly administering at spaced intervals with the administrations spaced by, e.g., a day, a week, a month, several months, or even years, the method is useful to detecting progressive thrombotic disease or responsiveness to therapeutic intervention.

Detection of thrombi with labelled α2AP polypeptides offers several advantages over convention detection approaches such as assays using fibrinogen. For example, since fibrinogen was historically purified from human sources, the conventional fibrinogen-based assay is no longer feasible due to the danger of HIV-contamination. Since the disclosed α2AP polypeptides are smaller than fibrinogen, they cane be administered in higher concentration (e.g., mM doses) than conventional diagnostic compounds. Their relatively small size also allows quicker clearance from the subject and a more favorable signal-to-noise ratio.

Other embodiments are within the following claims.

What is claimed is:

1. A method of detecting an actively forming blood clot in a mammal, comprising
   (a) administering to said mammal a diagnostically effective amount of a detectably labeled alpha-2 antiplasmin (α 2AP) polypeptide, comprising the amino acid sequence of $Xaa_1$ Gln $Xaa_2$ $Xaa_3$ $Xaa_4$ $Xaa_5$ Pro Leu $Xaa_6$ Leu Leu Lys (SEQ ID NO:1), wherein $Xaa_1$=Ala, $Xaa_2$=Glu or Gln, $Xaa_3$=Gln or Lys, $Xaa_4$=Val or Leu, $Xaa_5$=Pro or Ser, and $Xaa_6$=Thr, Ser or Ala; and
   (b) determining by in vivo imaging localization of said polypeptide, wherein localization at a site of a vascular obstruction indicates an actively forming blood clot compared to a pre-existing blood clot at said site.

2. The method of claim 1, wherein said polypeptide comprises the amino acid sequence of SEQ ID NO:6.

3. The method of claim 1, wherein the polypeptide comprises the amino acid sequence of SEQ ID NO:7.

4. The method of claim 1, wherein said α2AP polypeptide is biotinylated.

5. The method of claim 1, wherein said α2AP polypeptide is tagged with a radioisotope.

6. The method of claim 1, wherein said α2AP polypeptide is tagged with a gamma-emitter, positron-emitter, or an x-ray emitter.

7. The method of claim 1, wherein said α2AP polypeptide is tagged with a paramagnetic.

8. The method of claim 1, wherein said α2AP polypeptide is tagged with a radioisotope selected from the group consisting of $^{111}$In, $^{99m}$Tc, $^{125}$I, $^{67}$Ga, $^{68}$Ga, 157Gd, $^{55}$Mn, $^{162}$Dy, $^{52}$Cr, $^{56}$Fe, $^{97}$Ru, $^{72}$As, $^{89}$Zr, $^{90}$Y, and $^{201}$Tl.

* * * * *